United States Patent [19]
Saffran

[11] Patent Number: 5,660,225
[45] Date of Patent: Aug. 26, 1997

[54] METHOD OF FRACTURE TREATMENT BY RESTRAINING MACROMOLECULES OR MACROMOLECULAR AGGREGATES ADJACENT TO DAMAGED TISSUES

[76] Inventor: Bruce Nathan Saffran, 1527 Beacon St., #4, Brookline, Mass. 02146

[21] Appl. No.: 557,432

[22] Filed: Nov. 13, 1995

Related U.S. Application Data

[62] Division of Ser. No. 114,745, Aug. 30, 1993, Pat. No. 5,466,862.
[51] Int. Cl.⁶ ............................................. A61F 2/28
[52] U.S. Cl. .................. 623/16; 606/74; 128/898; 623/11
[58] Field of Search .............. 623/11, 16; 600/37; 128/898; 606/74, 70, 71, 69

[56] References Cited

U.S. PATENT DOCUMENTS

| | | | |
|---|---|---|---|
| 4,642,120 | 2/1987 | Nevo-Sui . | |
| 5,002,583 | 3/1991 | Pitaru-Sandu . | |
| 5,084,051 | 1/1992 | Tormala et al. | 623/13 |
| 5,443,483 | 8/1995 | Kirsch | 606/74 |

*Primary Examiner*—Robert A. H. Clarke

[57] ABSTRACT

The invention and the corresponding method of fracture stabilization provided is a malleable medication-containing device that is capable of both stabilizing fracture fragments and delivering medicines directly to fracture fragments when wrapped around or affixed to fractured tissues. This invention is designed to be used in conjunction with rigid fixation devices when rigid fixation is required of the major fragments. The novel device is comprised of two layers affixed to each other by chemical or mechanical means: a flexible, minimally-porous biologically-compatible fabric and a flexible biologically-compatible microporous polymer into which desired medications have been embedded. The preferred method of employment is to wrap the device around a fracture with the medication side in; and tighten it until the desired tension is achieved, thereby holding native fracture fragments in register. The medications imbedded in the microporous component subsequently diffuse in timed-release fashion from the microporous polymer directly into the fracture site. When the device is wrapped around or affixed to the fracture, the diffusion of embedded medicines is unidirectional. The minimally-porous surface, being relatively impermeable to macromolecules, directs the released medicine into the fracture site and away from surrounding tissues. The minimally-porous material can be made of any suitable fabric or polymer sheet such that, when affixed to the microporous layer, it is minimally permeable to macromolecules and can be manipulated by the surgeon at the time of use. Similarly, the microporous material can be of any suitable polymer such that, when affixed to the minimally-porous component, it can be made to contain and release into solution medications that can diffuse to the site of injury. The entire invention can, depending on the materials of which it is composed, either be removed surgically at a later time, or resorb in situ, over the course of weeks to months.

9 Claims, 6 Drawing Sheets

METHOD OF FRACTURE TREATMENT BY RESTRAINING MACROMOLECULES OR MACROMOLECULAR AGGREGATES ADJACENT TO DAMAGED TISSUES

This application is a divisional of U.S. Ser. No. 08/114,745 filed Aug. 30, 1993 now U.S. Pat. No. 5,466,262.

FIELD OF INVENTION

This invention relates to the treatment of fractured tissues within the human body, specifically to the way fractured tissues are apposed and drugs are delivered to promote healing.

BACKGROUND OF THE INVENTION

Traumatic injury to the human body is perhaps the single most important contributor to long-term disability among working-aged persons in the industrialized world. Although many tissues are commonly fractured in traumatic injury, e.g., the liver, the kidney, the spleen and the testicle, perhaps the most often-injured tissues are the bones. I will discuss this invention in light of the treatment of bone fractures, recognizing that this invention can be applied to the treatment of other fractured tissues under appropriate circumstances.

The goals of bone fracture treatment are to stabilize healing fragments in anatomic alignment while allowing movement of surrounding muscles, thereby minimizing muscular atrophy during healing. Simple, transverse fractures are the quickest to heal, and it is with these that orthopedic surgery has been the most successful. However when a bone is shattered, even in 1993, the result is often permanent deformity and long term disability.

The two classes of internal fixation devices, i.e., appliances that are affixed to bone and left in the body during healing, currently in use are cortical compression plates and intrameduallary rods. These devices are very similar to those used over a century ago, and consequently do not take full advantage of the advances in our understanding of bone biology. A third class of orthopedic devices, the implantable prosthetics, has also been proposed (see U.S. Pat. Nos. 4,642,120 to Nevo-Svi, 1987 and No. 5,002,583 to Pitaru-Sandu, 1991). These devices are designed to become incorporated into host tissue after their implantation. These devices do incorporate biologic growth factors into their design but, for reasons I will discuss below, suffer from several disadvantages and consequently are not in widespread use.

It was recognized in the late 1800s that bone fractures healed faster when the proximal and distal ends were apposed. The compression plate, first described by Hansmann in 1886, is a rigid flat metal bar that is secured across a fracture with screws. Since its introduction, numerous configurations of the compression plate have been designed to improve the quality of fixation; however, since all involve securing the fracture with one or more rigid plates bound to the bone cortex, the adverse effects of the device on host bone are many. Three deserve mention, as they are major concerns in clinical practice.

First, although adequate for simple transverse fractures, a plate is unable to secure shattered bone because fragments are often small size and "free-floating" within the fracture cavity. Furthermore, multiple bone fragments are naturally resorbed ((biodegraded by host enzymes such that they are converted to their molecular form) unless they are held rigidly together. Fragment resorption is perhaps the most significant obstacle to healing comminuted fractures. Second compression plates remove virtually all stress where they are affixed such that the hardest bone, the cortex, often resorbs and becomes "spongified" increasing the risk of refracture. This effect is most pronounced the longer the plate is in place. Third, the longer a foreign body, e.g., a fixation device, is in place the greater the risk for infection. For these reasons, most orthopedic surgeons agree that, although the compression plate is useful, the less time it is affixed to host bone the better.

Recently, a malleable plate has been introduced for use of fractures involving curved surfaces, e.g., acetabular fractures. This plate is similar to the rigid plate in that it is metal; however it can be bent to better approximate segments of a curved bone such as the pelvis. Although a major advance, the malleable plate suffers from several limitations. First, it uses screws to hold together only the major fragments of the fracture, leaving the small fragments free to resorb. Second, it is of no additional benefit in the treatment of long bone fractures; and for the reasons stated above it may be a liability. Third, when the malleable plate is used alone, bone fragments are not held together when forces perpendicular to the long axis of the plate are applied.

A second class of internal fixation appliances is the intramedullary rod. Rod fixation involves pounding a long nail through the center of the bone, the medullary cavity, such that it bridges the fracture site. The advantages of rod fixation are maintenance of alignment and limb length, at least while the rod is in place. Although widely used, the intramedullary rod is poorly suited for comminuted fractures. The rod displaces fragments and severely compromises their blood supply, often resulting in resorbed fragments and non union. Furthermore, since small fragments surrounding the rod often resorb, the patient has a defect between proximal and distal fracture segments. Surgical intervention is subsequently required for bone grafting to maintain limb length.

A third type of fixation device has been proposed, the implantable fixed prosthetic device (see U.S. Pat. No. 5,002,583 to Pitaru-Sandu, 1991). These devices are composed of a rigid core surrounded by collagen that, once in the body, forms a biological bond with and integrates into host tissues. Although potentially suitable for affixing a prosthetic device to native bone, this device is poorly suited for treatment of fractures for at least three reasons: First, the device is rigid, making it impossible to modify if in the operating room to suit a specific need. Surgeons rarely know exactly the extent and dimensions of tissue injury until a fracture is exposed. Second, since these devices form an irreversible bond with the host tissue, fracture fragments resorb, causing native tissue to be replaced with prosthetic. Native tissue is always preferable to prosthetic, unless it is cancerous or is severely arthritic. Finally, foreign material, no matter of what it is composed, dramatically increases the risk of infection by blood-borne bacteria. Orthopedic surgeons almost universally agree that the sooner all prostheses are removed, the better. Implantable prosthetics, however, remain in the body for life.

In the case of implantable gels, e.g., U.S. Pat. No. 4,642,120 to Nevo-Svi, 1987, the gel is provided as an amorphous jelly which contains biologically active molecules and/or living cells. These gels are unsuitable for fractures for several reasons, of which three deserve mention as they severely limit their use in clinical practice. First, gels, even if supplied as a paste are unable to tightly bind fragments together. Fragments are then free to "float" around the cavity and out of the plane formed by the major fracture fragments. This often causes deformity and limb shortening when and if the fracture heals. Second, if the gel "hardens" once in place, native fracture fragments will be hindered in their ability to bridge among themselves by the intervening prosthetic. Thus, native fragments will be replaced by prosthetic as in the fixed prosthetic described above. Third, cells and/or medications are free to diffuse from the gel in all directions, often causing heterotopic (in the wrong place) bone formation. If a gel fragment lodges between muscle strands and forms bone around it, this could limit the use of that muscle forever.

Unfortunately, despite a century of advances in orthopedic surgery, the healing of severe fractures often occurs years later, in poor anatomic alignment and with considerable heterotopic bone formation within neighboring soft tissues. The lack success in repairing comminuted fractures stems from the fact that the problems of fragment resorbtion, cortical weakening during prolonged fixation, and diminution of bone blood supply during fixation have still not been adequately addressed by currently available orthopedic devices. An ideal fixation device would:

1) Hold the native fragments of a fracture in register such that they do not resorb.
2) Deliver growth-promoting medications, e.g., bone morphogenetic proteins, angiogenic factors, nerve growth factors etc., directly and specifically to the injured tissues thereby preventing fragment resorbtion, and/or cell death, while minimizing reaction of neighboring tissues.
3) Permit the surgeon to manipulate the device into the most advantageous configuration while in the operating room.
4) Augment the function of and decrease the adverse effects (e.g., cortical "spongification") of existing classes of fixation devices such that fracture healing is quickened, permitting the rapid removal of fixation devices from the fracture site.
5) Minimize heterotopic bone formation in soft tissues surrounding the fracture.

This invention meets these conditions by providing a malleable fixation device that, when wrapped around or affixed to fractured tissues, holds the fragments in tight register while delivering any of a number of medications directly and specifically to the fracture site. This invention is designed to be used with existing orthopedic devices that provide rigid fixation of major fracture fragments. With this invention heterotopic bone formation will be minimized, since both the exogenous (supplied by the invention) and endogenous (supplied by the native healing tissue) growth factors are directed preferentially into the fracture site. This invention is provided as a flexible two layered sheet that the surgeon in the operating room can staple, suture or otherwise affix to the injured site as each particular case demands.

SUMMARY OF THE INVENTION

The invention and the corresponding method of fracture stabilization provided is a malleable medication-containing device that is capable of both stabilizing fracture fragments and delivering medicines directly to fracture fragments when wrapped around or affixed to fractured tissues. This invention is designed to be used in conjunction with rigid fixation devices when rigid fixation is required of the major fragments. The novel device is comprised of two layers affixed to each other by chemical or mechanical means: a flexible, minimally-porous biologically-compatible fabric and a flexible biologically compatible microporous polymer into which desired medications have been embedded. The preferred method of employment is to wrap the device around a fracture with the medication side in; and tighten it until the desired tension is achieved, thereby holding native fracture fragments in register. The medications imbedded in the microporous component subsequently diffuse in timed-release fashion from the microporous polymer directly into the fracture site. When the device is wrapped around or affixed to the fracture, the diffusion of embedded medicines is unidirectional. The minimally-porous surface, being relatively impermeable to macromolecules, directs the released medicine into the fracture site and away from surrounding tissues. The minimally-porous material can be made of any suitable fabric or polymer sheet such that, when affixed to the microporous layer, it is minimally permeable to macromolecules and can be manipulated by the surgeon at the time of use. Similarly, the microporous material can be of any suitable polymer such that, when affixed to the minimally-porous component, it can be made to contain and release into solution medications that can diffuse to the site of injury. The entire invention can, depending on the materials of which it is composed, either be removed surgically at a later time, or resorb (biodegrade) in situ, over the course of weeks to months.

BRIEF DESCRIPTION OF THE DRAWINGS

FIG. 1 is a side view of the malleable stabilization device wrapped around a comminuted bone fracture. "11" represents a minimally-porous biologically-compatible fabric. Note that in the preferred embodiment, it is internal to "12", "12" represents the flexible microporous polymer into which the desired medications have been embedded. "13" represents the intrafragmentary space into which medications embedded in the microporous polymer are to diffuse. "14" represents a fracture fragment. Note that the fragments are contained within the margins of and held in register by the invention. "15" represents a suture that can be used to tighten the invention around fracture fragments. Staples or belts may also be used for this purpose. "16" represents the major fragments of the tissue.

REFERENCE NUMERALS

11) Malleable, minimally-porous anchoring component
12) Malleable, microporous, medication-containing component
13) Intrafragmentary space
14) Tissue fragment
15) Tightening device (suture)
16) Major fragments of fracture
17) Free medicine within the intrafragmentary space
18) Micropore with medicine embedded within it
19) Empty micropore following effusion of embedded medicine

DETAILED DESCRIPTION OF THE INVENTION

The surgical fixation device of this invention comprises two components forming an integral structure: i) a malleable, minimally-porous anchoring component, "11" and ii) a malleable, microporous, medication-containing component, "12". These two components could be affixed to each other by chemical and/or mechanical means.

The Malleable, Minimally-Porous Anchoring Component:

The malleable, minimally-porous anchoring component, "11", consists of a flexible sheet of material that is biologically-compatible, and minimally porous to medicines imbedded in the microporous component. This preferred material is nylon; however it can be manufactured with any other material that meets the above criteria including but not limited to metal, a metal alloy, a plastic, a synthetic polymer, a biological polymer, or a biodegradable biological polymer. The thickness of the material is typically 0.1 mm to 2.5 mm. The dimensions are variable depending on the fracture being repaired; however for a comminuted femoral fracture the dimensions would be approximately 20 cm×10 cm. The polymer can be biodegradable or inert. The only requirements are that, at the time of employment, the material be:
1) biologically compatible and not prohibitively toxic during its tenure in the body.
2) malleable and can be bent and/or cut in the operating room.
3) minimally porous as described above.
4) That the polymer can be bound, either chemically or mechanically to the minimally-porous anchoring component.
5) strong enough to hold the microporous, medication-containing component tightly against the injured tissues.

The Microporous, Medication-Containing Component:

The microporous, medication-containing component, "12", consists of a biologically-compatible, flexible, polymer that has been solidified around a medication in such a way as to permit diffusion of medication from its pores (#17 and #18). There are numerous polymers that can be solidified in such a manner as to contain micropores that permit medications to diffuse from them. A representative and suitable compound is silicone; however it can be manufactured with any other material that meets the above criteria including but not limited to a synthetic polymer, a biological polymer, a resorbable biological polymer, a surgical gut, a gelatin and a collagen. For the purpose of describing the present invention, I will discuss how a protein can be embedded into a silicone matrix such that it can diffuse into solution over the course of days to weeks depending on the concentrations of materials used.

Solid silicone is dissolved in sufficient methylene chloride to form an even, completely liquid mixture. An aqueous (water-based) protein-containing solution is then added to the liquid silicone-methylene chloride mixture. Since the latter solution is hydrophobic and does not mix with the aqueous protein-containing solution, two layers are formed in the test tube. The test tube is then vigorously mixed for two minutes, preferably on a high-speed mixer. When the solution is being mixed, microscopic water bubbles containing protein become suspended in the liquid silicone-methylene chloride. This suspension is transferred immediately from the mixer to an ice-cold glass molding trough that has been placed on dry ice. Once the suspension is in the ice-cold molding trough, the solution will almost immediately become solid (frozen), trapping the minute "bubbles" of protein solution within the silicone-methylene chloride. The frozen mixture remains on the dry ice until the volatile methylene chloride evaporates (about an hour). What remains is solid silicone that has reformed around minute pockets of protein-containing water. The protein-containing silicone is then transferred to a desiccator to remove the water. After the water is drawn off, what remains is pure protein molecules trapped in the silicone micropores formed by the evaporated water. When implanted into aqueous environments, e.g., the human body, the polymer will slowly release the protein in a timed-release fashion according to the size of the pores and the concentration of the protein initially mixed into the aqueous solution (see FIGS. 2b and 2c).

Silicone is only one of several polymers that can be made to release medicine into solution in such a fashion. For the purposes of this invention, it does not matter which particular polymer is used, or which medication is embedded. The polymer can be biodegradable or inert. The thickness of the material is typically 5 mm to 15 mm. The dimensions are variable depending on the fracture being repaired; however for a comminuted femoral fracture the dimensions would be approximately 19 cm×9 cm. The only requirements for the microporous, medication-containing component are:
1) That the polymer be biologically compatible and not prohibitively toxic during its tenure in the body.
2) That the polymer is flexible and can be bent and/or cut in the operating room.
3) That the polymer release medications into solution.
4) That the polymer can be bound, either chemically or mechanically to the minimally-porous anchoring component.

Figure 1:
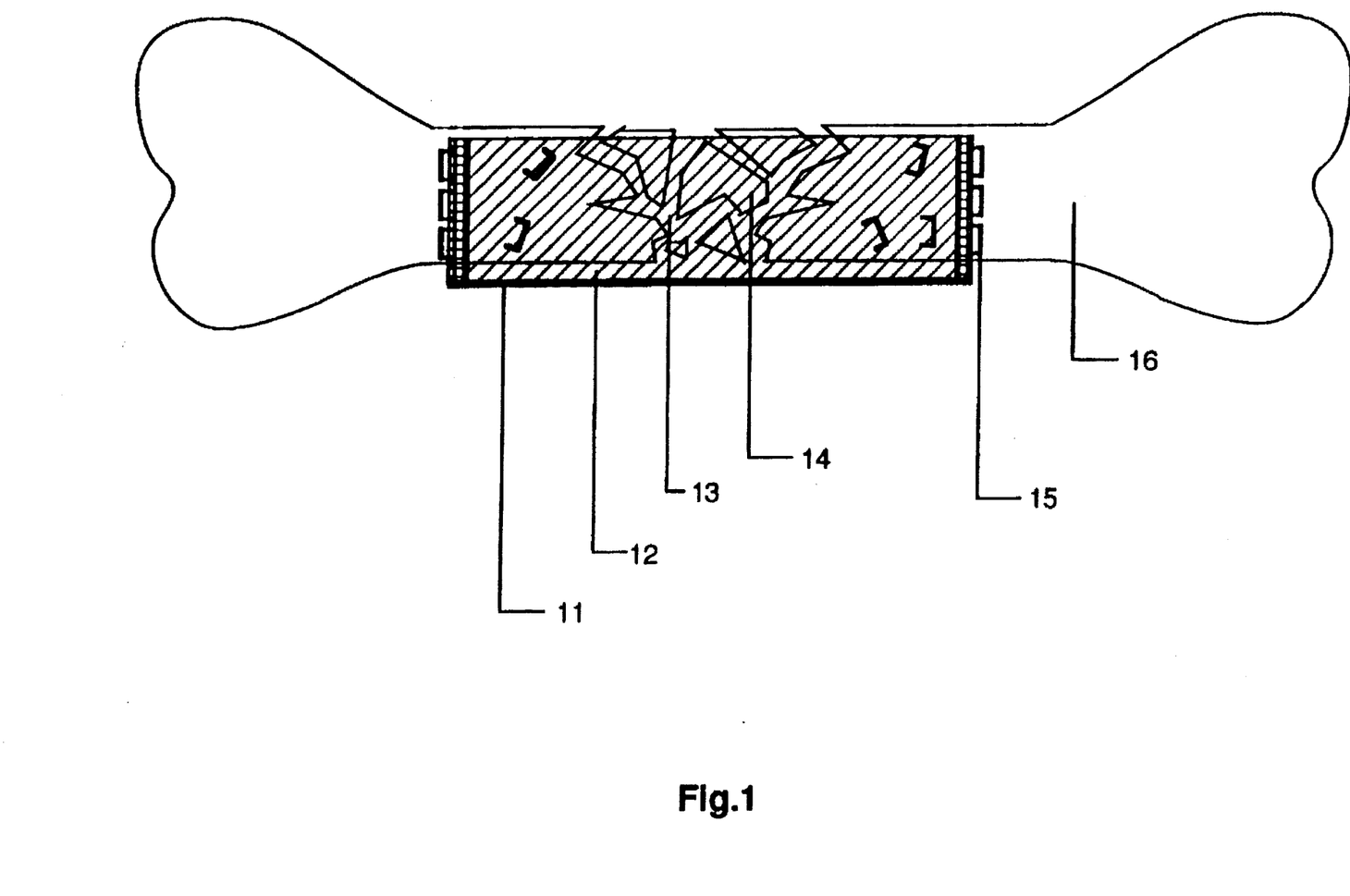
Figure 2A:
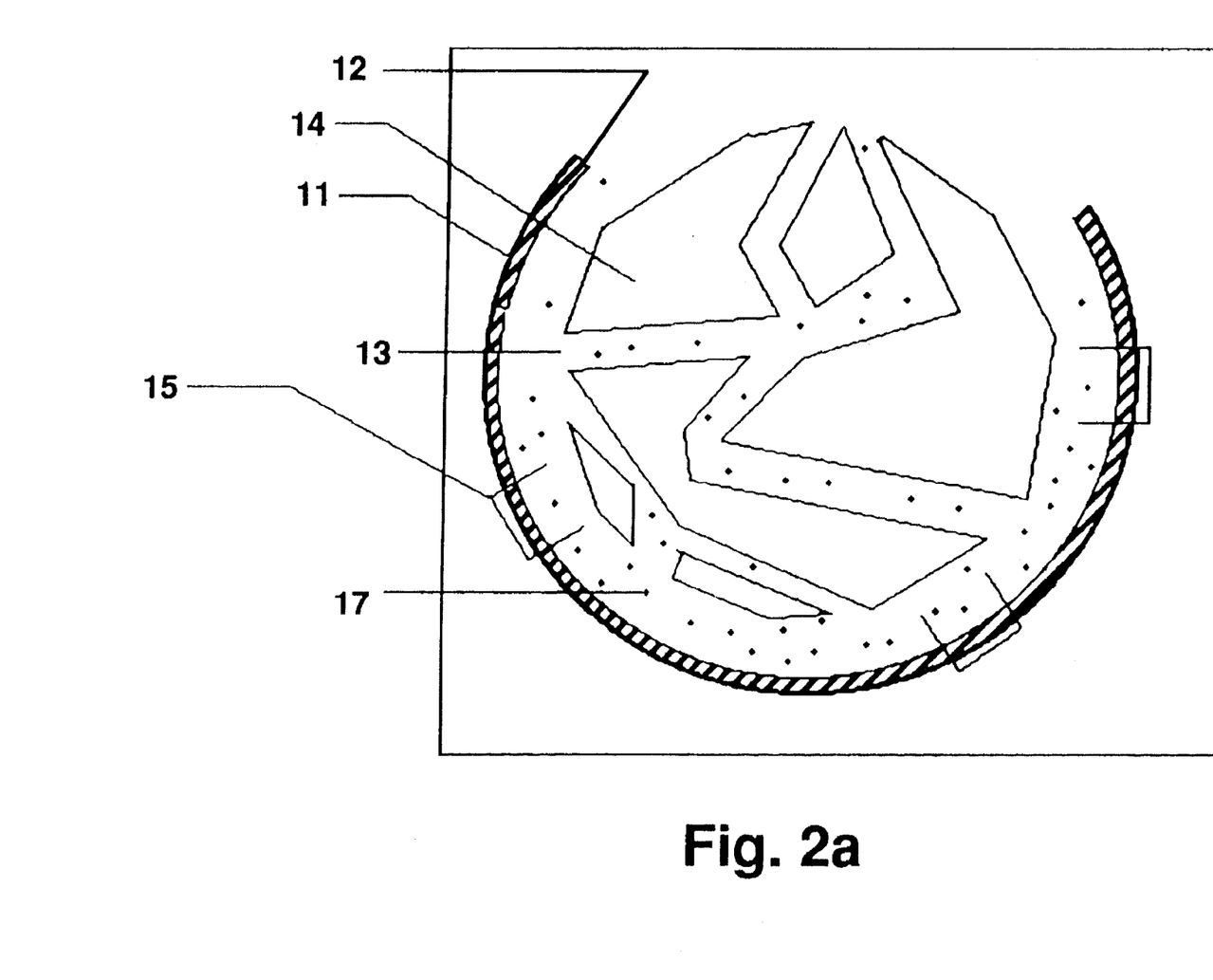
FIG. 2a is a cross-sectional view of the malleable stabilization device around the bone fragments taken at the dashed line, "A", bisecting FIG. 1. Note that the heavy line at the inferior margin of the invention in FIG. 1, labeled "1", is actually the profile of the minimally-porous component curving into the plane of the paper.
Figure 2B:
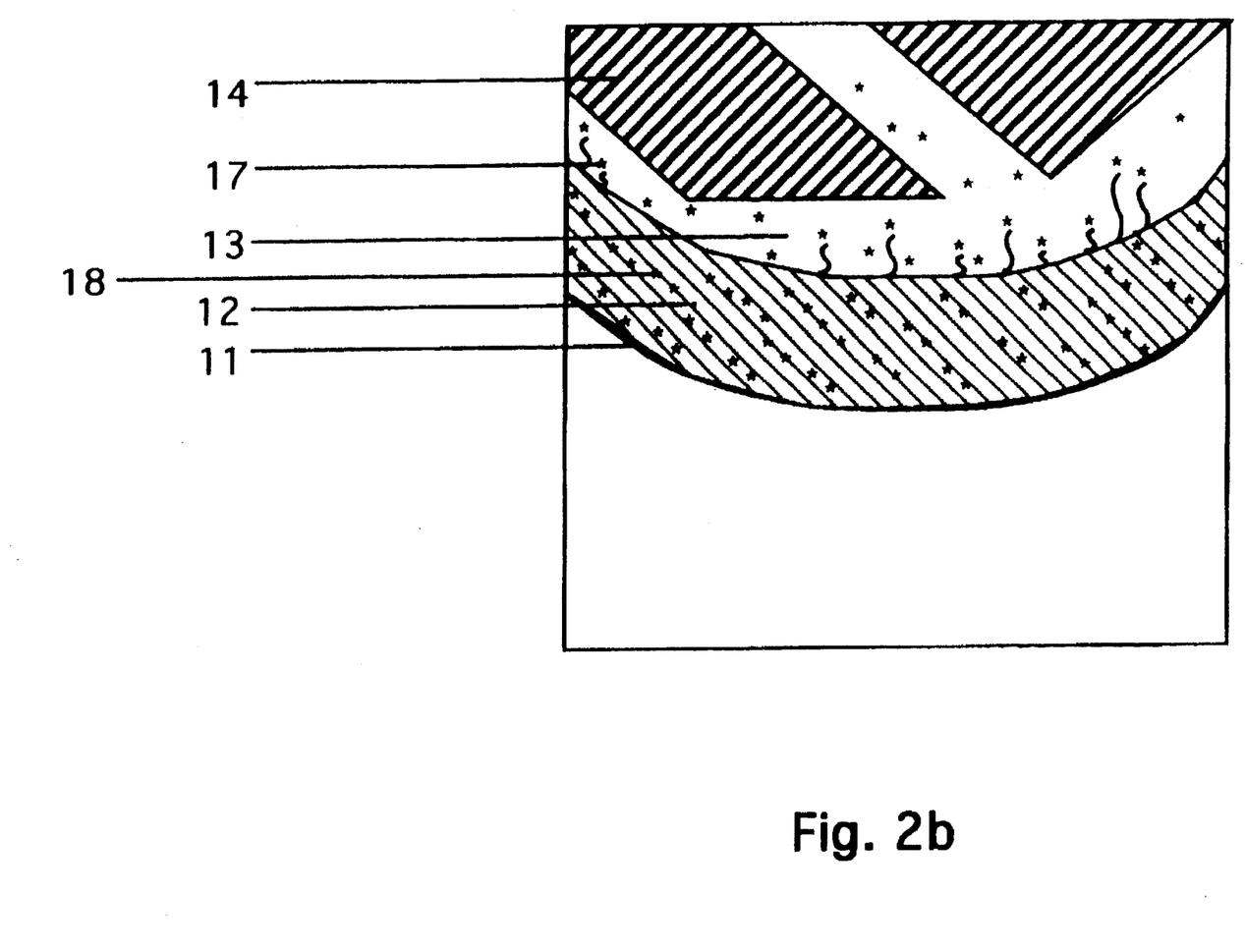
FIG. 2b is an magnified view of FIG. 2a taken of the boxed area showing the malleable stabilization device-bone interface in greater detail. Note that medicine embedded in the microporous component, "18", diffuses out of the polymer and becomes medicine within the intrafragmentary space, "17".
Figure 2C:
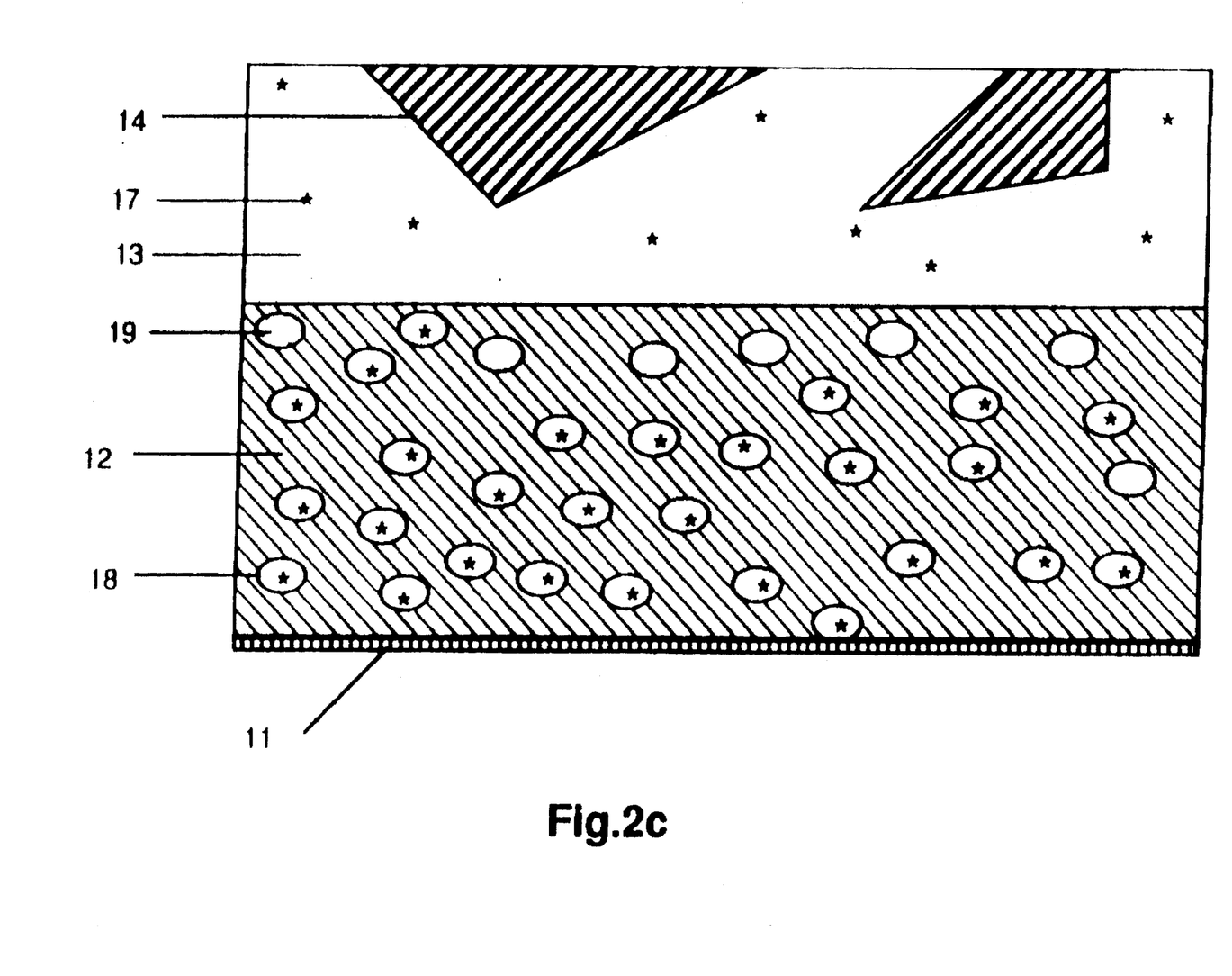
FIG. 2c is a magnified view of the boxed area of FIG. 2b showing in greater detail the medicine within the pores of the microporous component. Note that some of the superficial pores are empty, "19", the medicine that was contained within, "18", having diffused into the intrafragmentary space.
Figure 3A:
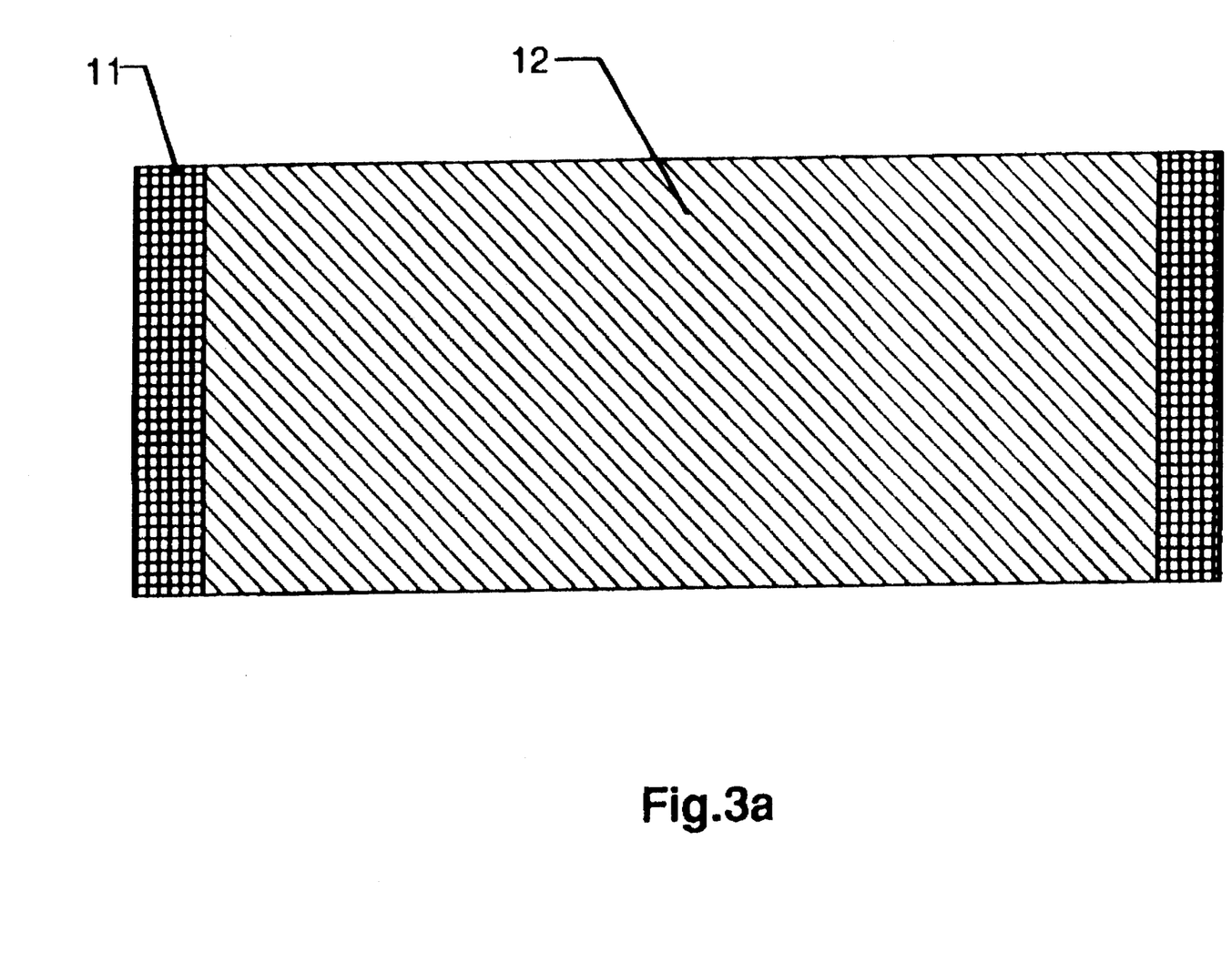
FIG. 3a is a side view of the malleable stabilization device prior to being affixed to a fracture by the surgeon.
Figure 3B:
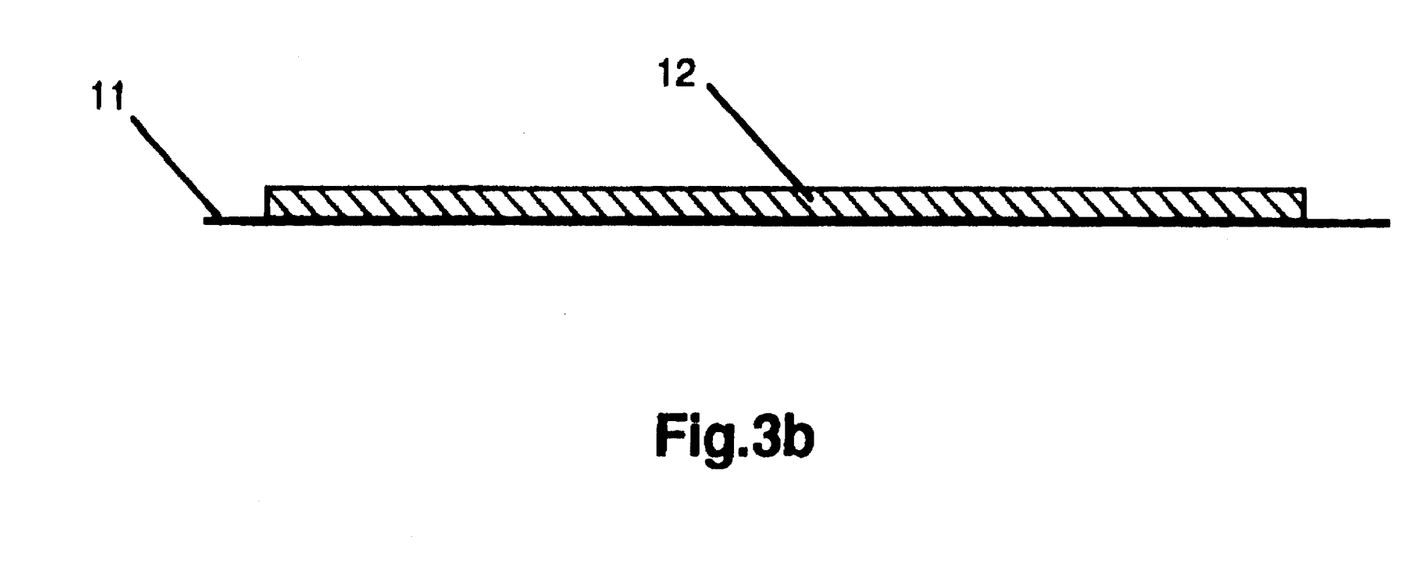
FIG. 3b is a top view of the malleable stabilization device in its unrolled position showing the minimally-porous anchoring component extending beyond the edge of the microporous medication-containing component.

Operation of the Malleable Fracture Stabilization Device:

FIGS. 1 and 2 show the malleable fracture stabilization device with micropores wrapped around a comminuted fracture of a long bone. The invention is to be provided as a sterile sheet (FIG. 3) with the two components already affixed and a specific medication or combination of medications already imbedded in it. Once affixed to the tissue, the overhanging portions of the minimally porous anchoring component would be affixed either to the host tissue or to their opposite counterpart as is illustrated in FIGS. 1 and 2a. A typical example of the circumstances of use of this invention is as follows:

A patient arrives in the emergency department after being hit by a car. X-rays of his right leg reveal a severely shattered right femur (thigh bone). An orthopedic surgeon takes the patient to the operating room to fix the fracture. He/she then exposes the fracture and elects to stabilize the major components of the fracture using an intramedularry rod. He/she then selects the malleable fracture stabilization device containing bone protein to stabilize and prevent resorbtion of the minor fragments. The malleable fracture stabilization device with micropores is to be provided as a sterile sheet (FIG. 3) with the two integral components already affixed and a specific medication or combination of medications already imbedded in it, in this case, bone morphogenetic protein. The surgeon selects the size of sheet according to the dimensions of the fracture. He/she then wraps the sheet around the fracture with the microporous, medication-containing component, "12", directed to the inside of the fracture (FIGS. 1 & 2). The surgeon then tightens and secures the device such that the fragments are held tightly together and in anatomic alignment. The size of sheet to be selected should be sufficient to overlap the ends of the major fragments both proximal and distal to the fracture fragments as is shown in FIG. 1.

The invention is to be provided in several different sizes, and with several different combinations of medications. In the operating room, the surgeon need only choose the appropriate size sheet and the preferred medications he/she wishes to deliver. The invention can be twisted, bent or cut to meet the exact requirements of the injury. The minimally-porous anchoring component provides the necessary strength to hold the malleable, microporous, medication-containing component tightly around or against the injured tissue. The surgeon then affixes the invention to the injured tissues using staples, sutures or bands according to his/her preference. This invention can, depending on the materials of which it is composed, either be removed surgically at a later time, or resorb (biodegrade) in situ, over the course of weeks to months.

The advantages to this arrangement are many: First, even in the absence of embedded medication, the invention will hold the small fragments tightly together and hold the small fragments tightly to the major fragments of the fracture. Second, when a medication such as bone morphogenetic protein is embedded, new bone spicules will rapidly bridge the minor fragments to each other and to the major fragments. Since both the exogenous (supplied by the invention) and endogenous (supplied by the native healing tissue) bone morphogenetic protein is directed preferentially into the fracture site by the minimally porous component, heterotopic bone formation will be minimized.

SUMMARY

From the above discussion, the reader will appreciate several advantages that my malleable fixation device has over the prior art. Specifically:

a) It is malleable. This invention combines the advantages of the malleable compression plate in that it can be bent and adjusted in the operating room to conform to fracture dimensions, with the additional benefit that small fragments can be held in register, maintaining anatomical alignment and preventing fragment resorption. Furthermore, the device can be wrapped around fragments rather than across a limited region of the fracture, advantageously decreasing the number of screws and screw holes placed in the bone.

b) It directs medications directly and preferentially into the fracture. This invention directs embedded medications preferentially into the fracture while simultaneously containing the endogenous substances released by healing tissues in the fracture cavity. This not only greatly increases the concentration of growth-promoting substances and other medications in the fracture site but additionally this invention limits the movement of these substances into heterotopic sites. Consequently, heterotopic tissue formation is minimized.

c) It encourages the reincorporating of native tissue rather than incorporation of prosthetic. This invention promotes the re-establishment of bridging between native fragments, rather than substitution of native fragments with a prosthetic device. The preferential maintenance of native tissue permits remodeling and strengthening of the fracture site to occur in a much more physiologic fashion than occurs with incorporated prosthetic.

d) It augments the function of and decreases the adverse effects of existing classes of fixation devices. By augmenting the function of existing devices, the fracture not only heals faster and with a better cosmetic and functional result, but it decreases the incidence of infection by permitting earlier removal of foreign bodies from the fracture site. Furthermore, surgical implementation of this invention is simple, keeping operating time and intraoperative morbidity to a minimum.

RAMIFICATIONS AND SCOPE

Accordingly, the reader will see that the malleable fixation device with micropores for directed drug delivery can be used to reduce the morbidity and socioeconomic costs that follow severe fractures of long bones. Although this invention has been applied to the treatment of bone fractures, this malleable fixation device could be used to treat fractures including but not limited to the liver, the spleen, the kidney, and the testicle depending on the medications employed and the size of the invention sheet used. For example, the invention could be manufactured in several shapes, such as circular, oval, trapezoidal, etc.; and could contain any of a number of medications including, but not limited to, bone morphogenetic proteins, nerve growth factors, extracellular matrix components, e.g., fibronectin and laminin, connective tissue growth factors such as fibroblast growth factors, antibiotics, vitamins, cofactors, and living cells—either wild-type or genetically engineered.

Thus the scope of the invention should be determined not only by the content of the above sections but also by the appended claims and their legal equivalents, rather than by the specific examples given.

Having thus described the invention and the process by which it is used in detail, what is claimed as new is:

1. A method of treating an injured tissue to promote healing in human or veterinary medicine comprising:

a) providing a device including,
      i) a first layer of flexible material that is minimally-porous to macromolecules, being capable of shaping in three dimensions by manipulation by human hands, having a first and second major surface, the first layer being substantially impermeable to at least one type of macromolecule or macromolecular aggregate,
      ii) a second layer of flexible material that is microporous being capable of shaping in three dimensions by manipulation by human hands, having a first and second major surface, the second layer having means for preventing the egress of at least one type of macromolecule or macromolecular aggregate, wherein the device being flexible in three dimensions by manipulation by human hands;

b) placing the device adjacent to the injured tissue such that at least a portion of the second layer is disposed closer to an outer portion of the injured tissue than any portion of the first layer;

whereby the placed device prevents the egress of at least one type of macromolecule or macromolecular aggregate.

2. The method of claim 1, wherein the first and second layers permit passage of at least one type of small molecule such that the concentration of the at least one small molecule when the device is placed against the damaged tissue are roughly equal adjacent to the injured tissue and tissue adjacent to the outermost portion of the first layer of the device.

3. The method of claim 1, wherein at least one treating material is affixed to the second layer such that the at least one treating material is introduced to the injured tissue.

4. The method of claim 3, wherein the at least one treating material is affixed to the second layer prior to placing the device adjacent the injured tissue.

5. A method of treating an injured tissue to promote healing in human or veterinary medicine comprising:

a) providing a device including,
  i) a first layer of flexible material that is minimally-porous to macromolecules, being capable of shaping in three dimensions by manipulation by human hands, having a first and second major surface, the first layer being substantially impermeable to at least one type of macromolecule or macromolecular aggregate,
  ii) a second layer of flexible material that is microporous being capable of shaping in three dimensions by manipulation by human hands, having a first and second major surface, the second layer having means for preventing the egress of at least one type of macromolecule or macromolecular aggregate, the second layer having material release means for release of at least one treating material in a directional manner the device being flexible in three dimensions by manipulation by human hands;

b) placing the device adjacent to the injured tissue such that at least a portion of the second layer is disposed closer to an outer portion of the injured tissue than any portion of the first layer;

whereby the placed device permits the egress of at least one treating material towards the injured tissue.

6. The method of claim 5, wherein the material release means includes a polymeric matrix.

7. A method of treating an injured tissue to promote healing in human or veterinary medicine comprising:

a) providing a device including,
  i) a first layer of flexible material that is minimally-porous to macromolecules, being capable of shaping in three dimensions by manipulation by human hands, having a first and second major surface, the first layer being substantially impermeable to at least one type of macromolecule or macromolecular aggregate,
  ii) a second layer of flexible material that is microporous being capable of shaping in three dimensions by manipulation by human hands, having a first and second major surface, the second layer having means for preventing the egress of at least one type of macromolecule or macromolecular aggregate, wherein the device being flexible in three dimensions by manipulation by human hands;

b) placing the device adjacent to the injured tissue such that at least a portion of the second layer is disposed closer to an outer portion of the injured tissue than any portion of the first layer;

whereby the placed device substantially restrains at least one type of macromolecule or macromolecular aggregate while permitting the passage of cellular waste products, glucose, and oxygen, such that the concentration of each when the device is placed against the damaged tissue are roughly equal in the outer layer of the injured tissue and tissue adjacent to the outermost portion of the first layer.

8. The method of claim 7, wherein at least one treating material is affixed to the second layer such that the at least one treating material is introduced to the injured tissue.

9. The method of claim 8, wherein the at least one treating material is affixed to the second layer prior to placing the device adjacent the injured tissue.

* * * * *